(12) United States Patent
Neri et al.

(10) Patent No.: US 8,455,625 B2
(45) Date of Patent: Jun. 4, 2013

(54) FUSION PROTEIN OF ANTIBODY L19 AGAINST FIBRONECTIN ED-B AND INTERLEUKIN 12

(75) Inventors: Dario Neri, Buchs (CH); Verena Gafner, Bern (CH); Cornelia Halin, Zurich (CH)

(73) Assignee: Philogen S.p.A., Siena (IT)

( * ) Notice: Subject to any disclaimer, the term of this patent is extended or adjusted under 35 U.S.C. 154(b) by 350 days.

(21) Appl. No.: 11/913,483

(22) PCT Filed: May 3, 2006

(86) PCT No.: PCT/EP2006/004114
§ 371 (c)(1),
(2), (4) Date: Nov. 2, 2007

(87) PCT Pub. No.: WO2006/119897
PCT Pub. Date: Nov. 16, 2006

(65) Prior Publication Data
US 2009/0035255 A1 Feb. 5, 2009

Related U.S. Application Data

(60) Provisional application No. 60/680,105, filed on May 11, 2005.

(51) Int. Cl.
| | |
|---|---|
| *C07K 16/30* | (2006.01) |
| *C07K 16/46* | (2006.01) |
| *C07K 14/54* | (2006.01) |
| *C07H 21/04* | (2006.01) |
| *C12N 5/16* | (2006.01) |
| *C12N 1/21* | (2006.01) |
| *C12N 15/63* | (2006.01) |
| *C12N 15/24* | (2006.01) |
| *A61P 35/00* | (2006.01) |

(52) U.S. Cl.
USPC ............... 530/387.7; 435/69.52; 435/69.7; 435/252.3; 435/328; 435/330; 514/13.3; 514/19.3; 530/387.3; 530/399; 536/23.4

(58) Field of Classification Search
None
See application file for complete search history.

(56) References Cited

U.S. PATENT DOCUMENTS 6,838,260 B2   1/2005  Gillies et al.
2002/0193570 A1 * 12/2002  Gillies et al. .................. 530/351

FOREIGN PATENT DOCUMENTS

WO   99/29732   6/1999

OTHER PUBLICATIONS

Wells (1990) Biochemistry 29(37): 8509-8517.*

(Continued)

*Primary Examiner* — Zachary Howard
(74) *Attorney, Agent, or Firm* — Patrick J. Hagan; Dann, Dorfman, Herrell and Skillman, P.C.

(57) ABSTRACT

Conjugate for targeting therapeutic or diagnostic agent or drug to cells or tissues in a body, e.g. areas of neoplastic growth or angiogenesis. Use of conjugate for in vivo diagnosis or therapy e.g. inhibiting tumor growth or metastasis, inhibiting angiogenesis and/or treating cancer. Conjugate comprises therapeutic or diagnostic agent as oligomeric protein e.g. heterodimeric protein, wherein first and second subunits of protein are each conjugated to a specific binding member e.g. an antibody fragment such as scFv. Subunits of oligomer may be conjugated to specific binding members as fusion proteins. Conjugate may comprise IL-12 heterodimer having two subunits, each subunit fused to scFv L19 or TN11 for targeting IL-12 to extracellular matrix components associated with neoplastic growth and angiogenesis.

13 Claims, 7 Drawing Sheets

OTHER PUBLICATIONS

Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Haisma et al, 1998. Blood. 92: 184-190.*
Neri et al, 1998. Advanced Drug Delivery Reviews. 31: 43-52.*
Ferrer-Costa (2007. J Mol Biol. 365: 249-256).*
Yoon et al (2000). The EMBO Journal. 19(14): 3530-3541.*
Pignatelli et al, 1990; Proc Natl Acad Sci USA, 87: 1541-1545.*
V. Gafner et al., "An engineered antibody-interleukin-12 fusion protein with enhanced tumor vascular targeting properties", Int. J. Cancer, 119: 2205-2212 (2006).
C. Heuser et al., "Anti-CD30-IL Antibody-Cytokine Fusion Protein that Induces IFN-T Secretion of T Cells and NK Cell-Mediated Lysis of Hodgkin's Lymphoma-Derived Tumor Cells", Int. J. Cancer, 106: 545-552 (2003).
K. Makabe et al., "Tumor-directed lymphocyte-activating cytokines: refolding-based preparation of recombinant human interleukin-12 and an antibody variable domain-fused protein by additive-introduced stepwise dialysis", Biochenm. Biophys. Res. Comm., 328(1): 98-105 (2005).
L. Peng et al., "A Single-Chain IL-12 IgG3 Antibody Fusion Protein Retains Antibody Specificity and IL-12 Bioactivity and Demonstrates Antitumor Activity", J. Immunol., 163: 250-258 (1999).
A. Van Spriel et al., "Immunotherapeutic perspective for bispecific antibodies", Immunol. Today, 21(8): 391-397 (2000).
Borsi, L. et al., "Selective targeted delivery of TNFalpha to tumor blood vessels", Blood, 102(13): 4384-4392 (2003).
Borsi, L. et al., "Selective Targeting of Tumoral Vasculature: Comparison of Different Formats of an Antibody (L19) to the ED-B Domain of Fibronectin", Int. J. Cancer, 102: 75-85 (2002).
Carnemolla, B. et al., "Enhancement of the antitumor properties of interleukin-2 by its targeted delivery to the tumor blood vessel extracellular matrix", Blood, 99(5): 1659-1665 (2002).
Halin, C. et al., "Synergistic Therapeutic Effects of a Tumor Targeting Antibody Fragment, Fused to Interleukin 12 and to Tumor Necrosis Factor alpha", Cancer Research, 63: 3202-3210 (2003).
Halin, C. et al., "Enhancement of the antitumor activity of interleukin-12 by targeted delivery to neovasculature", Nature Biotechnology, 20: 264-269 (2002).
King, D. et al., "Phase I Clinical Trial of the Immunocytokine EMD 273063 in Melanoma Patients", Journal of Clinical Oncology, 22(22): 4463-4473 (2004).
Ko, Y. et al., "Safety, Pharmacokinetics, and Biological Pharmacodynamics of the Immunocytokine EMD 273066 (huKS-IL2)", J. Immunother., 27(3): 232-239 (2004).
Neal, Z. et al., "Enhanced Activity of Hu14.18-IL2 Immunocytokine against Murine NXS2 Neuroblastoma when Combined with Interleukin 2 Therapy", Clinical Cancer Research, 10: 4389-4347 (2004).
Santimaria, M. et al., "Immunoscintigraphic Detection of the ED-B Domain of Fibronectin, a Marker of Angiogenesis, in Patients with Cancer", Clinical Cancer Research, 5: 571-579 (2003).

* cited by examiner

Signal peptide-human p40-linker-L19-myc-3x stop

MCHQQLVISWFSLVFLASPLVAIWELKKDVYVVELDWYPDAPGEMVVLTCDTPEEDG
ITWTLDQSSEVLGSGKTLTIQVKEFGDAGQYTCHKGGEVLSHSLLLLHKKEDGIWST
DILKDQKEPKNKTFLRCEAKNYSGRFTCWWLTTISTDLTFSVKSSRGSSDPQGVTCG
AATLSAERVRGDNKEYEYSVECQEDSACPAAEESLPIEVMVDAVHKLKYENYTSSFF
IRDIIKPDPPKNLQLKPLKNSRQVEVSWEYPDTWSTPHSYFSLTFCVQVQGKSKREK
KDRVFTDKTSATVICRKNASISVRAQDRYYSSSWSEWASVPCSGSADGGEVQLLESG
GGLVQPGGSLRLSCAASGFTFSSFSMSWVRQAPGKGLEWVSSISGSSGTTYYADSVK
GRFTISRDNSKNTLYLQMNSLRAEDTAVYYCAKPFPYFDYWGQGTLVTVSSGDGSSG
GSGGASEIVLTQSPGTLSLSPGERATLSCRASQSVSSSFLAWYQQKPGQAPRLLIYY
ASSRATGIPDRFSGSGSGTDFTLTISRLEPEDFAVYYCQQTGRIPPTFGQGTKVEIK
EQKLISEEDLN***

Figure 8

Signal peptide-L19-linker-human p35-6xHis-3x stop

GDNDIHFAFLSTGVHSEVQLLESGGGLVQPGGSLRLSCAASGFTFSSFSMSWVRQAP
GKGLEWVSSISGSSGTTYYADSVKGRFTISRDNSKNTLYLQMNSLRAEDTAVYYCAK
PFPYFDYWGQGTLVTVSSGDGSSGGSGGASEIVLTQSPGTLSLSPGERATLSCRASQ
SVSSSFLAWYQQKPGQAPRLLIYYASSRATGIPDRFSGSGSGTDFTLTISRLEPEDF
AVYYCQQTGRIPPTFGQGTKVEIKGSADGGRNLPVATPDPGMFPCLHHSQNLLRAVS
NMLQKARQTLEFYPCTSEEIDHEDITKDKTSTVEACLPLELTKNESCLNSRETSFIT
NGSCLASRKTSFMMALCLSSIYEDLKMYQVEFKTMNAKLLMDPKRQIFLDQNMLAVI
DELMQALNFNSETVPQKSSLEEPDFYKTKIKLCILLHAFRIRVTIDRVMSYLNASHH
HHHH***

CDR1                             CDR2

EVQLLESGGGLVQPGGSLRLSCAASGFTFS<u>SFSMS</u>WVRQAPGKGLEWVS<u>SISGSSGTTYYADSVKG</u>RFT

CDR3

ISRDNSKNTLYLQMNSLRAEDTAVYYCAK<u>PFPYFDY</u>WGQGTLVTVSS

LINKER

GDGSSGGSGGAS

VL                                  CDR1                              CDR2

EIVLTQSPGTLSLSPGERATLSC<u>RASQSVSSSFLA</u>WYQQKPGQAPRLLIY<u>YASSRAT</u>GIPDRFSGS

CDR3

GSGTDFTLTISRLEPEDFAVYYC<u>QQTGRIPPT</u>FGQGTKVEIK

```
SEQUENCE LISTING

<160> NUMBER OF SEQ ID NOS: 30

<210> SEQ ID NO 1
<211> LENGTH: 581
<212> TYPE: PRT
<213> ORGANISM: Artificial Sequence
<220> FEATURE:
<223> OTHER INFORMATION: Synthetic sequence: Fusion protein Signal
      peptide - human p40 - linker - L19 - myc

<400> SEQUENCE: 1

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
```

-continued

```
                100                 105                 110
Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Ser Ala Asp Gly Gly Glu Val
                325                 330                 335

Gln Leu Leu Glu Ser Gly Gly Gly Leu Val Gln Pro Gly Gly Ser Leu
            340                 345                 350

Arg Leu Ser Cys Ala Ala Ser Gly Phe Thr Phe Ser Ser Phe Ser Met
        355                 360                 365

Ser Trp Val Arg Gln Ala Pro Gly Lys Gly Leu Glu Trp Val Ser Ser
    370                 375                 380

Ile Ser Gly Ser Ser Gly Thr Thr Tyr Tyr Ala Asp Ser Val Lys Gly
385                 390                 395                 400

Arg Phe Thr Ile Ser Arg Asp Asn Ser Lys Asn Thr Leu Tyr Leu Gln
                405                 410                 415

Met Asn Ser Leu Arg Ala Glu Asp Thr Ala Val Tyr Tyr Cys Ala Lys
            420                 425                 430

Pro Phe Pro Tyr Phe Asp Tyr Trp Gly Gln Gly Thr Leu Val Thr Val
        435                 440                 445

Ser Ser Gly Asp Gly Ser Gly Gly Ser Gly Gly Ala Ser Glu Ile
    450                 455                 460

Val Leu Thr Gln Ser Pro Gly Thr Leu Ser Leu Ser Pro Gly Glu Arg
465                 470                 475                 480

Ala Thr Leu Ser Cys Arg Ala Ser Gln Ser Val Ser Ser Ser Phe Leu
                485                 490                 495

Ala Trp Tyr Gln Gln Lys Pro Gly Gln Ala Pro Arg Leu Leu Ile Tyr
            500                 505                 510

Tyr Ala Ser Ser Arg Ala Thr Gly Ile Pro Asp Arg Phe Ser Gly Ser
        515                 520                 525
```

-continued

Gly Ser Gly Thr Asp Phe Thr Leu Thr Ile Ser Arg Leu Glu Pro Glu
530                 535                 540

Asp Phe Ala Val Tyr Tyr Cys Gln Gln Thr Gly Arg Ile Pro Pro Thr
545                 550                 555                 560

Phe Gly Gln Gly Thr Lys Val Glu Ile Lys Glu Gln Lys Leu Ile Ser
                565                 570                 575

Glu Glu Asp Leu Asn
            580

<210> SEQ ID NO 2
<211> LENGTH: 460
<212> TYPE: PRT
<213> ORGANISM: Artificial Sequence
<220> FEATURE:
<223> OTHER INFORMATION: Synthetic sequence: Fusion protein Signal
      peptide- L19 - linker - human p35 - 6xHis

<400> SEQUENCE: 2

Gly Asp Asn Asp Ile His Phe Ala Phe Leu Ser Thr Gly Val His Ser
1               5                   10                  15

Glu Val Gln Leu Leu Glu Ser Gly Gly Gly Leu Val Gln Pro Gly Gly
            20                  25                  30

Ser Leu Arg Leu Ser Cys Ala Ala Ser Gly Phe Thr Phe Ser Ser Phe
        35                  40                  45

Ser Met Ser Trp Val Arg Gln Ala Pro Gly Lys Gly Leu Glu Trp Val
50                  55                  60

Ser Ser Ile Ser Gly Ser Ser Gly Thr Thr Tyr Tyr Ala Asp Ser Val
65                  70                  75                  80

Lys Gly Arg Phe Thr Ile Ser Arg Asp Asn Ser Lys Asn Thr Leu Tyr
                85                  90                  95

Leu Gln Met Asn Ser Leu Arg Ala Glu Asp Thr Ala Val Tyr Tyr Cys
            100                 105                 110

Ala Lys Pro Phe Pro Tyr Phe Asp Tyr Trp Gly Gln Gly Thr Leu Val
        115                 120                 125

Thr Val Ser Ser Gly Asp Gly Ser Ser Gly Gly Ser Gly Gly Ala Ser
130                 135                 140

Glu Ile Val Leu Thr Gln Ser Pro Gly Thr Leu Ser Leu Ser Pro Gly
145                 150                 155                 160

Glu Arg Ala Thr Leu Ser Cys Arg Ala Ser Gln Ser Val Ser Ser Ser
                165                 170                 175

Phe Leu Ala Trp Tyr Gln Gln Lys Pro Gly Gln Ala Pro Arg Leu Leu
            180                 185                 190

Ile Tyr Tyr Ala Ser Ser Arg Ala Thr Gly Ile Pro Asp Arg Phe Ser
        195                 200                 205

Gly Ser Gly Ser Gly Thr Asp Phe Thr Leu Thr Ile Ser Arg Leu Glu
210                 215                 220

Pro Glu Asp Phe Ala Val Tyr Tyr Cys Gln Gln Thr Gly Arg Ile Pro
225                 230                 235                 240

Pro Thr Phe Gly Gln Gly Thr Lys Val Glu Ile Lys Gly Ser Ala Asp
                245                 250                 255

Gly Gly Arg Asn Leu Pro Val Ala Thr Pro Asp Pro Gly Met Phe Pro
            260                 265                 270

Cys Leu His His Ser Gln Asn Leu Leu Arg Ala Val Ser Asn Met Leu
        275                 280                 285

Gln Lys Ala Arg Gln Thr Leu Glu Phe Tyr Pro Cys Thr Ser Glu Glu
    290                 295                 300

```
Ile Asp His Glu Asp Ile Thr Lys Asp Lys Thr Ser Thr Val Glu Ala
305                 310                 315                 320

Cys Leu Pro Leu Glu Leu Thr Lys Asn Glu Ser Cys Leu Asn Ser Arg
            325                 330                 335

Glu Thr Ser Phe Ile Thr Asn Gly Ser Cys Leu Ala Ser Arg Lys Thr
            340                 345                 350

Ser Phe Met Met Ala Leu Cys Leu Ser Ser Ile Tyr Glu Asp Leu Lys
        355                 360                 365

Met Tyr Gln Val Glu Phe Lys Thr Met Asn Ala Lys Leu Leu Met Asp
    370                 375                 380

Pro Lys Arg Gln Ile Phe Leu Asp Gln Asn Met Leu Ala Val Ile Asp
385                 390                 395                 400

Glu Leu Met Gln Ala Leu Asn Phe Asn Ser Glu Thr Val Pro Gln Lys
                405                 410                 415

Ser Ser Leu Glu Glu Pro Asp Phe Tyr Lys Thr Lys Ile Lys Leu Cys
            420                 425                 430

Ile Leu Leu His Ala Phe Arg Ile Arg Val Thr Ile Asp Arg Val Met
            435                 440                 445

Ser Tyr Leu Asn Ala Ser His His His His His
450                 455                 460

<210> SEQ ID NO 3
<211> LENGTH: 306
<212> TYPE: PRT
<213> ORGANISM: Homo sapiens

<400> SEQUENCE: 3

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65              70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220
```

-continued

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
            245                 250                 255

Gly Lys Ser Lys Arg Glu Lys Lys Asp Arg Val Phe Thr Asp Lys Thr
        260                 265                 270

Ser Ala Thr Val Ile Cys Arg Lys Asn Ala Ser Ile Ser Val Arg Ala
    275                 280                 285

Gln Asp Arg Tyr Tyr Ser Ser Trp Ser Glu Trp Ala Ser Val Pro
290                 295                 300

Cys Ser
305

<210> SEQ ID NO 4
<211> LENGTH: 196
<212> TYPE: PRT
<213> ORGANISM: Homo sapiens

<400> SEQUENCE: 4

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Val Thr Ile Asp Arg Val Met Ser Tyr
            180                 185                 190

Leu Asn Ala Ser
    195

<210> SEQ ID NO 5
<211> LENGTH: 236
<212> TYPE: PRT
<213> ORGANISM: Artificial Sequence
<220> FEATURE:
<223> OTHER INFORMATION: Synthetic sequence: scFv(L19)

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Gly Thr Thr Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
            100                 105                 110

Thr Val Ser Ser Gly Asp Gly Ser Ser Gly Gly Ser Gly Gly Ala Ser
            115                 120                 125

Glu Ile Val Leu Thr Gln Ser Pro Gly Thr Leu Ser Leu Ser Pro Gly
    130                 135                 140

Glu Arg Ala Thr Leu Ser Cys Arg Ala Ser Gln Ser Val Ser Ser Ser
145                 150                 155                 160

Phe Leu Ala Trp Tyr Gln Gln Lys Pro Gly Gln Ala Pro Arg Leu Leu
                165                 170                 175

Ile Tyr Tyr Ala Ser Ser Arg Ala Thr Gly Ile Pro Asp Arg Phe Ser
            180                 185                 190

Gly Ser Gly Ser Gly Thr Asp Phe Thr Leu Thr Ile Ser Arg Leu Glu
        195                 200                 205

Pro Glu Asp Phe Ala Val Tyr Tyr Cys Gln Gln Thr Gly Arg Ile Pro
    210                 215                 220

Pro Thr Phe Gly Gln Gly Thr Lys Val Glu Ile Lys
225                 230                 235

<210> SEQ ID NO 6
<211> LENGTH: 33
<212> TYPE: DNA
<213> ORGANISM: Artificial sequence
<220> FEATURE:
<223> OTHER INFORMATION: Synthetic sequence: Primer sp40backEco

<400> SEQUENCE: 6
ccggaattca tgtgtcctca gaagctaacc atc                              33

<210> SEQ ID NO 7
<211> LENGTH: 48
<212> TYPE: DNA
<213> ORGANISM: Artificial sequence
<220> FEATURE:
<223> OTHER INFORMATION: Synthetic sequence: Primer L19stopNotfor

<400> SEQUENCE: 7
ttttcctttt gcggccgcct atcatcattt gatttccacc ttggtccc              48

<210> SEQ ID NO 8
<211> LENGTH: 35
<212> TYPE: DNA
<213> ORGANISM: Artificial sequence
<220> FEATURE:
<223> OTHER INFORMATION: Synthetic sequence: Primer sp40backHind

<400> SEQUENCE: 8
ccgtaaagct tatgtgtcct cagaagctaa ccatc                            35

<210> SEQ ID NO 9
<211> LENGTH: 33
<212> TYPE: DNA

<213> ORGANISM: Artificial sequence
<220> FEATURE:
<223> OTHER INFORMATION: Synthetic sequence: Primer L19forAgeIBsp

<400> SEQUENCE: 9
tgtgggaccg gttttgattt ccaccttggt ccc    33

<210> SEQ ID NO 10
<211> LENGTH: 33
<212> TYPE: DNA
<213> ORGANISM: Artificial sequence
<220> FEATURE:
<223> OTHER INFORMATION: Synthetic sequence: Primer HindSp40back

<400> SEQUENCE: 10
cccaagctta tgtgtcctca gaagctaacc atc    33

<210> SEQ ID NO 11
<211> LENGTH: 35
<212> TYPE: DNA
<213> ORGANISM: Artificial sequence
<220> FEATURE:
<223> OTHER INFORMATION: Synthetic sequence: Primer Sp40HaLifor

<400> SEQUENCE: 11
acctccatca gcgcttccgg atcggaccct gcagg    35

<210> SEQ ID NO 12
<211> LENGTH: 38
<212> TYPE: DNA
<213> ORGANISM: Artificial sequence
<220> FEATURE:
<223> OTHER INFORMATION: Synthetic sequence: Primer LinkL19back

<400> SEQUENCE: 12
ggaagcgctg atggaggtga ggtgcagctg ttggagtc    38

<210> SEQ ID NO 13
<211> LENGTH: 57
<212> TYPE: DNA
<213> ORGANISM: Artificial sequence
<220> FEATURE:
<223> OTHER INFORMATION: Synthetic sequence: Primer L19mycstoBamfor

<400> SEQUENCE: 13
attcagatcc tcttctgaga tgagtttttg ttctttgatt ccaccttgg tcccttg    57

<210> SEQ ID NO 14
<211> LENGTH: 45
<212> TYPE: DNA
<213> ORGANISM: Artificial sequence
<220> FEATURE:
<223> OTHER INFORMATION: Synthetic sequence: Primer mycstoBamfor

<400> SEQUENCE: 14
cgcggatccc tatcatcaat tcagatcctc ttctgagatg agttt    45

<210> SEQ ID NO 15
<211> LENGTH: 6
<212> TYPE: PRT
<213> ORGANISM: Artificial sequence
<220> FEATURE:
<223> OTHER INFORMATION: Synthetic sequence: Peptide linker

<400> SEQUENCE: 15

Gly Ser Ala Asp Gly Gly
1               5

-continued

<210> SEQ ID NO 16
<211> LENGTH: 28
<212> TYPE: DNA
<213> ORGANISM: Artificial sequence
<220> FEATURE:
<223> OTHER INFORMATION: Synthetic sequence: Primer EcoLonSL19back

<400> SEQUENCE: 16
ccggaattcg cttgtcgacc atgggctg                                      28

<210> SEQ ID NO 17
<211> LENGTH: 39
<212> TYPE: DNA
<213> ORGANISM: Artificial sequence
<220> FEATURE:
<223> OTHER INFORMATION: Synthetic sequence: Primer L19HaLifor

<400> SEQUENCE: 17
acctccatca gcgcttcctt tgatttccac cttggtccc                           39

<210> SEQ ID NO 18
<211> LENGTH: 39
<212> TYPE: DNA
<213> ORGANISM: Artificial sequence
<220> FEATURE:
<223> OTHER INFORMATION: Synthetic sequence: Primer HaLip35back

<400> SEQUENCE: 18
ggaagcgctg atggaggtag ggtcattcca gtctctgga                           39

<210> SEQ ID NO 19
<211> LENGTH: 36
<212> TYPE: DNA
<213> ORGANISM: Artificial sequence
<220> FEATURE:
<223> OTHER INFORMATION: Synthetic sequence: Primer p35hisfor

<400> SEQUENCE: 19
gtgatggtga tgatgatggg cggagctcag atagcc                              36

<210> SEQ ID NO 20
<211> LENGTH: 48
<212> TYPE: DNA
<213> ORGANISM: Artificial sequence
<220> FEATURE:
<223> OTHER INFORMATION: Synthetic sequence: Primer p35hisstoNotIfor

<400> SEQUENCE: 20
ttttcctttt gcggccgcct atcatcagtg atggtgatga tgatgggc                 48

<210> SEQ ID NO 21
<211> LENGTH: 249
<212> TYPE: PRT
<213> ORGANISM: Artificial Sequence
<220> FEATURE:
<223> OTHER INFORMATION: Synthetic sequence: anti-tenascin-C scFv(TN11)

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Arg Ile Thr Ile Phe Gly Gly Ala Phe Asp Ile
            100                 105                 110

Trp Gly Arg Gly Thr Met Val Thr Val Ser Ser Gly Gly Gly Gly Ser
            115                 120                 125

Gly Gly Gly Gly Ser Gly Gly Gly Ser Gln Ser Val Leu Thr Gln
        130                 135                 140

Pro Ala Ser Val Ser Gly Ser Pro Gly Gln Ser Ile Thr Ile Ser Cys
145                 150                 155                 160

Thr Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Gly Ser
            180                 185                 190

Lys Arg Pro Ser Gly Val Ser Asn Arg Phe Ser Gly Ser Lys Ser Gly
            195                 200                 205

Asn Thr Ala Ser Leu Thr Ile Ser Gly Leu Gln Ala Glu Asp Glu Ala
        210                 215                 220

Asp Tyr Tyr Cys Ser Ser Tyr Thr Thr Arg Ser Thr Arg Val Phe Gly
225                 230                 235                 240

Gly Gly Thr Lys Leu Thr Val Leu Gly
            245

<210> SEQ ID NO 22
<211> LENGTH: 116
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Phe
                20                  25                  30

Ser Met Ser Trp Val Arg Gln Ala Pro Gly Lys Gly Leu Glu Trp Val
            35                  40                  45

Ser Ser Ile Ser Gly Ser Ser Gly Thr Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
            100                 105                 110

Thr Val Ser Ser
        115

<210> SEQ ID NO 23
<211> LENGTH: 108
<212> TYPE: PRT
<213> ORGANISM: Homo sapiens

<400> SEQUENCE: 23

Glu Ile Val Leu Thr Gln Ser Pro Gly Thr Leu Ser Leu Ser Pro Gly
```

```
                1               5                   10                  15
Glu Arg Ala Thr Leu Ser Cys Arg Ala Ser Gln Ser Val Ser Ser Ser
                    20                  25                  30

Phe Leu Ala Trp Tyr Gln Gln Lys Pro Gly Gln Ala Pro Arg Leu Leu
                    35                  40                  45

Ile Tyr Tyr Ala Ser Ser Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
 65                     70                  75                  80

Pro Glu Asp Phe Ala Val Tyr Tyr Cys Gln Gln Thr Gly Arg Ile Pro
                    85                  90                  95

Pro Thr Phe Gly Gln Gly Thr Lys Val Glu Ile Lys
                100                 105

<210> SEQ ID NO 24
<211> LENGTH: 12
<212> TYPE: PRT
<213> ORGANISM: Artificial Sequence
<220> FEATURE:
<223> OTHER INFORMATION: Synthetic sequence: Peptide linker

<400> SEQUENCE: 24

Gly Asp Gly Ser Ser Gly Gly Ser Gly Gly Ala Ser
 1               5                  10

<210> SEQ ID NO 25
<211> LENGTH: 5
<212> TYPE: PRT
<213> ORGANISM: Homo sapiens

<400> SEQUENCE: 25

Ser Phe Ser Met Ser
 1               5

<210> SEQ ID NO 26
<211> LENGTH: 17
<212> TYPE: PRT
<213> ORGANISM: Homo sapiens

<400> SEQUENCE: 26

Ser Ile Ser Gly Ser Ser Gly Thr Thr Tyr Tyr Ala Asp Ser Val Lys
 1               5                  10                  15

Gly

<210> SEQ ID NO 27
<211> LENGTH: 7
<212> TYPE: PRT
<213> ORGANISM: Homo sapiens

<400> SEQUENCE: 27

Pro Phe Pro Tyr Phe Asp Tyr
 1               5

<210> SEQ ID NO 28
<211> LENGTH: 12
<212> TYPE: PRT
<213> ORGANISM: Homo sapiens

<400> SEQUENCE: 28

Arg Ala Ser Gln Ser Val Ser Ser Ser Phe Leu Ala
 1               5                  10
```

```
<210> SEQ ID NO 29
<211> LENGTH: 7
<212> TYPE: PRT
<213> ORGANISM: Homo sapiens

<400> SEQUENCE: 29

Tyr Ala Ser Ser Arg Ala Thr
1               5

<210> SEQ ID NO 30
<211> LENGTH: 9
<212> TYPE: PRT
<213> ORGANISM: Homo sapiens

<400> SEQUENCE: 30

Gln Gln Thr Gly Arg Ile Pro Pro Thr
1               5
```

FUSION PROTEIN OF ANTIBODY L19 AGAINST FIBRONECTIN ED-B AND INTERLEUKIN 12

CROSS-REFERENCE TO RELATED APPLICATIONS

This application is the U.S. National Stage of International Application No. PCT/EP2006/004114, filed 3 May 2006, which claims priority from U.S. Provisional Application No. 60/680,105, filed 11 May 2005. The entire disclosures of the aforesaid applications are incorporated by reference in the present application.

This invention relates to targeting of a drug to a desired in vivo site by conjugation to a target-specific specific binding member. The invention is especially directed to conjugates between IL 12 and antibody molecules for therapeutic applications such as inhibition of pathological angiogenesis, including treatment of cancer and other tumours, rheumatoid arthritis, diabetic retinopathy, age-related macular degeneration and angiomas.

The heterodimeric cytokine interleukin-12 (IL12) is a key mediator of innate and cellular immunity with potent antitumor and antimetastatic activity [4-6]. It is currently (Spring 2005) being tested in Phase II clinical trials for the treatment of cancer and infectious diseases. IL12 acts primarily on T and NK cells, stimulating their activity and the secretion of interferon-γ (IFN-γ) [7]. As with many other cytokines, however, the administration of recombinant human IL12 is associated with severe toxicity, even at doses as low as 1 μg/kg/day [8, 9], hampering its development as an anti-cancer drug.

A targeted delivery of IL12 to the tumour environment may be used to increase the therapeutic index of the cytokine.

Scientists at Lexigen have described the fusion of cytokines such as IL2 and IL12 to immunoglobulins in order to specifically target the cytokine [17, 49-51]. However, we, the present inventors, believe that there are limitations to such approaches. We recognise that IgG-cytokine fusions are in reality multi-functional proteins, and so in addition to antigen binding and cytokine activity, these IgG-based fusion proteins can activate complement and interact with Fc receptors. In our opinion this is an undesired property of IgG-cytokine fusions, as cytokines may be brought in proximity of cells (such as macrophage, neutrophils and natural-killer cells) carrying Fc receptors, thus hindering tumour targeting and causing non-specific cell activation. We consider it more desirable to use an antibody molecule lacking Fc, such as a single-chain Fv antibody fragment (scFv), instead of the full immunoglobulin.

We have previously demonstrated in rodent models of cancer that the therapeutic potential of IL12 can be considerably increased by fusing a single-chain polypeptide which sequentially encodes the subunits p40 and p35 of the murine cytokine IL12 ("scIL12") with the human single-chain Fv antibody fragment L19 ("scFv(L19)"). ScFv(L19) has been shown to be capable of selective tumour targeting in patients with cancer [16]. L19 specifically binds the ED-B domain of fibronectin isoform B-FN, which is one of the best known markers angiogenesis [14, 25]. ED-B is an extra domain of 91 amino acids found in the B-FN isoform and is identical in mouse, rat, rabbit, dog and man. B-FN accumulates around neovascular structures in aggressive tumours and other tissues undergoing angiogenesis, such as the endometrium in the proliferative phase and some ocular structures in pathological conditions, but is otherwise undetectable in normal adult tissues [1-3].

The fusion protein scIL12-scFv(L19) exhibited a therapeutic index far superior to scIL12 fused to a scFv of irrelevant specificity in mouse, and to recombinant murine IL12. These experiments clearly demonstrated the potential of antibody-based cytokine fusion proteins as an avenue for improving the therapeutic potential of IL12 [15]. The therapeutic potential of these results is considerable.

Targeting of IL12 at the level of tumour blood vessels, such as using L19, is therapeutically beneficial for a number of reasons. First, the tumour neovasculature is more accessible to intravenously-administered therapeutic agents than are tumour cells, which helps avoid problems associated with the interstitial hypertension of solid tumours [10]. Second, angiogenesis (the growth of new capillaries from pre-existing blood vessels) is a characteristic feature of the majority of aggressive solid tumours [11]. Targeting IL12 to the neovasculature should allow the immunotherapy of a variety of different tumour types. Third, IL12 shows an anti-angiogenic activity, conferred by its down-stream mediator IP-10 [12, 13].

We have already extensively studied the tumour targeting performance of scIL12-scFv(L19), and also that of scFv (L19) fused to another anti-tumour cytokine, IL2 ("scFv (L19)-IL2") [18]. ScFv(L19)-IL2 displays an excellent tumour-targeting performance in tumour-bearing mice, with tumour:blood and tumour:organ ratios as high as 30:1 twenty-four hours after intravenous injection. By contrast, the tumour-targeting ability of scIL12-scFv(L19) in the same animal models is more modest, with tumour:blood and tumour:organ ratios generally worse than 10:1 at 24 h, and with poor tumour:liver and tumour:spleen ratios [15]. These targeting results were nevertheless superior compared to a fusion protein scIL12-scFv(HyHEL10), specific to hen egg lysozyme but devoid of antigen-specific recognition in the mouse.

The tumour targeting properties of scFv(L19) have been shown to be improved when scFv(L19) was dimerised through a CH4 domain of human IgE, building a mini-antibody structure, also termed "small immune protein" or SIP. The tumour targeting properties of SIP(L19) have been previously described [21].

The present invention is based on work in which we, the inventors, compared tumour-targeting abilities of three conjugates of IL12 and scFv(L19) each having a different format of the cytokine and/or of the antibody, and found that the tumour-targeting ability of scIL12-scFv(L19) could be improved by changing the format of the conjugate in a particular way.

One format we tested was scIL12-scFv(L19), illustrated in FIG. 1A. This conjugate showed modest tumour-targeting ability, consistent with the prior art findings.

Another format utilised the dimeric SIP(L19) construct mentioned above to create a homodimer of scIL12-SIP(L19), illustrated in FIG. 1B. However, despite the prior art indication that tumour-targeting properties of L19 could be improved using the SIP format, we did not observe an increased tumour uptake of this conjugate.

Another format was a heterodimer of IL12 p40 and p35 subunits, in which each subunit was fused to scFv(L19), forming a scFv(L19)-p35/p40-scFv(L19) heterodimer as illustrated in FIG. 1C. With this heterodimeric format we achieved a marked improvement in tumour uptake of the conjugate.

Thus, we have discovered that a new antibody-IL12 fusion protein format, consisting of two scFv fragments heterodimerised via the p40 and p35 subunits of IL12, retains full IL12 activity and displays an excellent tumour-targeting ability.

These results have significant therapeutic implications for improved targeting of IL 12 to tumours and to other sites of pathological angiogenesis, e.g., for treating rheumatoid arthritis, diabetic retinopathy, age-related macular degeneration and angiomas. The usefulness of this invention extends not only to the fusion of IL 12 to scFv(L19), but also to conjugates between other specific binding members and other drugs and substances. For example, conjugates may be constructed with specific binding members other than scFv(L19) conjugated to IL 12 subunits, such as other antibody fragments specific for tumour-associated antigens e.g. isoforms of tenascin-C, and used for tumour targeting and cancer therapy. The wider implications also include a variety of other applications involving targeting of substances in vivo, including diagnostic methods as well as the prevention and treatment of diseases and other pathological conditions.

The invention in various aspects relates to the new conjugates, methods of producing them, nucleic acids encoding the conjugates or components thereof, pharmaceutical compositions containing the conjugates, and use of the conjugates in methods of treatment.

In one aspect, the invention is a conjugate comprising a protein having first and second subunits, wherein the first and second subunits are each conjugated to a specific binding member.

The protein is generally dimeric, preferably heterodimeric, and typically comprises a biologically active agent or drug, normally a therapeutic or diagnostic agent.

Thus, the conjugate normally has the following format:

[specific binding member]-[first subunit]-[second subunit]-[specific binding member]

The specific binding members are normally antibody molecules, preferably single chain Fv (scFv). Single chain Fv (scFv) antibody molecules are particularly preferred in the present invention owing to their small size, which provides physiological and therapeutic advantages for in vivo use of the conjugates. In addition, scFv lack an Fc region, potentially reducing anti-idiotypic reactions and also minimising undesirable properties relating to activation of complement and interaction with Fc receptors that may hinder tumour targeting and cause non-specific cell activation.

Thus, a preferred format of the conjugate is:

[ScFv]-[first subunit]-[second subunit]-[ScFv]

Alternatively, the specific binding member may be a single domain antibody, and/or an antibody fragment. Specific binding members and antibody molecules are described in more detail below.

The conjugate may be or may comprise a fusion protein, i.e. a polypeptide that is a translation product resulting from the fusion of two or more genes or nucleic acid coding sequences into one open reading frame (ORF). The fused expression products of the two genes or ORFs may be conjugated by a peptide linker (a short 2-20, preferably 2-15, residue stretch of amino acids). In one embodiment the peptide linker is a 6-residue sequence GSADGG (SEQ ID NO: 15). The fusion protein may comprise signal peptide sequence, normally located upstream (5') of the specific binding member and subunit.

In conjugates of the invention, the first and second subunits are generally linked, for instance they may be covalently linked, e.g. through one or more disulphide bonds. The protein may be oligomeric (e.g. dimeric, preferably heterodimeric), and may occur naturally in oligomeric form, and thus the first and second subunits in the conjugate may associate with each other in their natural way. The invention therefore allows use and maintenance of a natural format of the protein in the conjugate. This avoids any need to construct or use a single-chain variant of the drug and maximises the potential for the drug to retain its full activity in the conjugate. In addition, conjugation between the subunits allows the conjugate to be conveniently constructed and assembled by allowing the first and second subunits to associate (e.g. dimerise) in the oligomer. Thus, typically the first and second subunits may each be conjugated to a specific binding member, forming a pair of specific binding member-subunit constructs (e.g. heterodimers) that associate through the subunits. In a preferred embodiment, the first subunit is conjugated to a specific binding member as a first fusion protein, and the second subunit is conjugated to a specific binding member as a second fusion protein.

Preferably, the conjugate has a molecular weight of 250 kDa or less, more preferably 200 kDa, 150 kDa, 125 kDa, 120 kDa or 115 kDa or less (i.e. an Mr of or less than 250 000, 200 000, 150 000, 125 000, 120 000 or 115 000). This may be the actual measured molecular weight (with or without glycosylation), or an estimated value based on e.g. the expected molecular weight of the conjugate (with or, normally, without) glycosylation. A relatively small size of the conjugate increases its ability to penetrate tissues and access the target site (e.g. site of angiogenesis, tumour or disease), thus increasing its therapeutic efficacy and reducing the dosage required, while still achieving a multivalent (generally bivalent) binding of the conjugate to the target.

In general, the protein and the specific binding member are selected according to the intended use of the conjugate. In a preferred embodiment, the protein is IL12. As discussed above, IL12 is suitable for treating cancer, inhibiting tumour growth and metastasis, and for treating other conditions associated with pathological angiogenesis. One or both specific binding members in a conjugate may specifically bind a marker associated with neoplastic (especially tumour) growth and/or angiogenesis, e.g. a marker located at the site of neoplastic growth and/or angiogenesis. Extracellular matrix components may be markers of neoplastic growth and/or angiogenesis, because the extracellular matrix is remodelled during these processes.

One example is the B-FN isoform of fibronectin which, as explained above, contains an extra domain ED-B. A specific binding member of the invention preferably binds specifically to ED-B of fibronectin isoform B-FN. The specific binding member may have an amino acid sequence comprising the VH CDR1 (SEQ ID NO: 25), VH CDR2 (SEQ ID NO: 26) and/or VH CDR3 (SEQ ID NO: 27) sequences of L19 and/or the VL CDR1 (SEQ ID NO: 28), VL CDR2 (SEQ ID NO: 29) and/or VL CDR 3 (SEQ ID NO: 30) sequences of L19. For example, the specific binding member may be an scFv having a VH domain with an amino acid sequence comprising VH CDR1, VH CDR2 and/or VH CDR3 of L19, and a VL domain with an amino acid sequence comprising VL CDR1, VL CDR2 and/or VL CDR3 of L19. A specific binding member may comprise a VH domain having an amino acid sequence with at least 60%, 65%, 70%, 75%, 80%, 85%, 90%, 95% or 100% sequence identity with the amino acid sequence of the L19 VH domain as set out in SEQ ID NO: 22, and/or comprises a VL domain having an amino acid sequence with at least 60%, 65%, 70%, 75%, 80%, 85%, 90%, 95% or 100% sequence identity with the amino acid sequence of the L19 VL domain as set out in SEQ ID NO: 23. Preferably the specific binding member is an scFv(L19) comprising an L19 VH domain (SEQ ID NO: 22) and an L19 VL domain (SEQ ID NO: 23). In a preferred embodiment, the specific binding member is scFv(L19) having the amino acid sequence SEQ ID NO: 5 (FIG. 10).

Another example is tenascin-C (TnC), which exists in various isoforms. In neoplastic tissues TnC containing additional domains are more widely expressed than in normal tissues, especially isoforms containing domain C (cTN-C) [33]. Thus, a specific binding member in conjugates of the invention may specifically bind tenascin-C isoforms associated with neoplastic tissues, especially cTN-C. The specific binding member may be TN11 scFv having a sequence as set out in SEQ ID NO: 21 (FIG. 11) [33].

The specific binding member in conjugates of the invention may alternatively bind other tumour-associated antigens, i.e. antigens more prevalent in a tumour environment (such as on a tumour cell) than in a normal cellular environment (such as on non-tumour cells).

Normally, the two specific binding members in a conjugate are identical, or are at least both specific for the same target, antigen or epitope.

In a particularly preferred embodiment of the invention, the conjugate comprises a human IL12 heterodimer conjugated to and between two specific binding members, preferably scFv(L19); wherein
  the heterodimer has a first (normally p40) subunit and a second (normally p35) subunit;
  the first or p40 subunit is conjugated to a first specific binding member as a first fusion protein;
  the second or p35 subunit is conjugated to a second specific binding member as a second fusion protein.

As noted above, the first and second subunits are typically covalently linked e.g. disulphide bonded.

Preferably, the first or p40 subunit is fused N-terminal to the specific binding member, i.e. the subunit is upstream of the specific binding member in the fusion protein and in the nucleic acid encoding it. In this form, the N-terminus of p40 can therefore be free (unfused), which is believed to maximise its activity.

Preferably, the second or p35 subunit is fused C-terminal to the specific binding member, i.e. the subunit is downstream of the specific binding member in the fusion protein and in the nucleic acid encoding it. This may enhance expression of the fusion protein, because the specific binding member, especially with an upstream N-terminal signal peptide, may be easily expressed and thus allow efficient expression of the fusion protein.

Preferably, the first fusion protein has the amino acid sequence of p40-scFv(L19) as shown in SEQ ID NO: 1. Preferably, the second fusion protein has the amino acid of scFv(L19)-p35 as shown in SEQ ID NO: 2.

Conjugates of the invention may be produced in any available method, e.g. using recombinant techniques, for example by expressing all or part of the conjugate as a fusion protein.

For example, a conjugate may be produced in a method comprising:
  expressing a first fusion protein comprising the first subunit and a specific binding member;
  expressing a second fusion protein comprising the second subunit and a specific binding member; and
  conjugating the first and second subunits together.

Normally the method comprises purifying the first and second fusion proteins after expression.

Normally the expression is performed in a host cell containing nucleic acid encoding the fusion protein, e.g. a cultured eukaryotic cell such as HEK or a CHO cell, or a bacterial cell such as *Escherichia coli*. Expression may therefore comprise culturing such a host cell. Where the first and second fusion proteins are expressed in the same cell (e.g. a cell co-transfected with or containing nucleic acids encoding the two fusion proteins), heterodimerisation or oligomerisation of the subunits may occur in the cell or during purification of the fusion proteins from the cell. In other cases, the first and second fusion proteins may be expressed separately (e.g. in different cells) and then brought together (combined) such that the first and second subunits heterodimerise or otherwise associate.

Conjugating the subunits together may be an active or passive process. Conjugating may comprise exposing or subjecting the first and second fusion proteins to conditions in which the first and second subunits are conjugated together (e.g. associate or oligomerise/heterodimerise). Conjugating may comprise disulphide bond formation between the subunits, or formation of another covalent linkage. Conjugation such as disulphide bond formation may occur under non-reducing conditions, and therefore conjugating may comprise exposing the first and second fusion proteins to non-reducing conditions.

Suitable methods for expressing fusion proteins and producing conjugates according to the invention are given in detail in the Examples below.

As a further step, the method may comprise formulating the conjugate into a pharmaceutical composition. Generally this involves purifying the conjugate and combining it with a physiologically acceptable carrier. Pharmaceutical compositions are described in more detail below.

Nucleic acid molecules encoding the conjugates and parts thereof (e.g. encoding fusion proteins) also form part of the invention.

In one aspect the invention is a composition comprising
  a first nucleic acid molecule comprising a nucleotide sequence encoding a fusion protein, wherein the fusion protein comprises a specific binding member and a first protein subunit; and
  a second nucleic acid molecule comprising a nucleotide sequence encoding a fusion protein, wherein the fusion protein comprises a specific binding member and a second protein subunit.

The nucleic acid molecule may encode a peptide linker between the specific binding member and the subunit, such that in the fusion protein the specific binding member and subunit are joined by the peptide linker. Particular fusion proteins, subunits, specific binding member and linkers that may be encoded are described in more detail elsewhere herein. In a preferred embodiment the first and second subunits are IL12 heterodimeric subunits (typically p40 and p35 subunits), respectively, and preferably the specific binding member is an scFv, especially scFv(L19). In one embodiment the first nucleic acid molecule encodes the amino acid sequence of IL12p40-scFv(L19) as set out in SEQ ID NO: 1 and/or the second nucleic acid molecule encodes the amino acid sequence of scFv(L19)-IL12p35 as set out in SEQ ID NO: 2.

The nucleic acid molecule may be a vector, e.g. a plasmid suitable for expression of the nucleotide sequence. Thus, the first and second nucleic acid molecules may be first and second vectors. Normally the nucleotide sequence is operably linked to a regulatory element such as a promoter for transcription.

The first and second nucleic acid molecules may be contained in a host cell, which may be a cell co-transfected with the nucleic acid molecules or a daughter of such a cell. Cells, especially eukaryotic cells e.g. HEK and CHO cells, or bacterial cells e.g. *Escherichia coli*, containing the nucleic acid molecules also form part of the invention.

After expression from the nucleic acids, the fusion proteins may be conjugated through the subunits to form conjugates of the invention, as described elsewhere herein.

Conjugates according to the invention may be used in a method of treatment of the human or animal body, such as a method of treatment (which may include prophylactic treatment) of a disease or disorder in a patient (typically a human patient) comprising administering the conjugate to the patient.

Conditions treatable using the conjugates include cancer, other tumours and neoplastic conditions. The conjugates may be used to inhibit angiogenesis and thereby treat rheumatoid arthritis, diabetic retinopathy, age-related macular degeneration, angiomas and tumours, including cancer. Treatment may include prophylactic treatment. The conjugates may also be administered in diagnostic methods, e.g. targeting and diagnosis of angiogenesis, which may be associated with any of the above conditions. Other diseases and conditions may also be diagnosed and treated, according to the nature of the protein therapeutic or diagnostic agent contained in the conjugate, and the specificity of the specific binding member.

Accordingly, further aspects of the invention provide methods of treatment comprising administering a conjugate of the invention, pharmaceutical compositions comprising such a conjugate, and use of such a conjugate in the manufacture of a medicament for treatment of a condition or disease, for example in a method of making a medicament or pharmaceutical composition comprising formulating the conjugate with a physiologically acceptable carrier or excipient.

In accordance with the invention, compositions provided may be administered to a patient. Administration is preferably in a "therapeutically effective amount", this being sufficient to show benefit to the patient. Such benefit may be at least amelioration of at least one symptom. The actual amount administered, and rate and time-course of administration, will depend on the nature and severity of what is being treated. Prescription of treatment, e.g. decisions on dosage etc, is within the responsibility of general practitioners and other medical doctors. Appropriate doses of antibody are well known in the art [26, 27].

Conjugates of the invention, including those comprising an antibody antigen-binding domain, may be administered to a patient in need of treatment via any suitable route, usually by injection into the bloodstream and/or directly into the site to be treated, e.g. tumour or tumour vasculature. The precise dose and its frequency of administration will depend upon a number of factors, the route of treatment, the size and location of the area to be treated (e.g. tumour), the precise nature of the antibody (e.g. scFv molecule), and the nature of any detectable label or other molecule contained in the conjugate.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opiates such as morphine, or anti-emetics.

Thus pharmaceutical compositions according to the present invention, and for use in accordance with the present invention, may comprise, in addition to active ingredient (conjugate), a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous. For intravenous injection, or injection at the site of affliction, the active ingredient will be in the form of a parenterally acceptable aqueous solution which is pyrogen-free and has suitable pH, isotonicity and stability.

In conjugates of the invention, the protein normally comprises recombinantly produced first and second polypeptide subunits. The subunits may be glycosylated, and the degree and nature of such glycosylation may be controlled by selection of an appropriate host cell in which to express the subunits. The protein may comprise a biologically active agent, i.e. an agent that affects the structure or functioning of a subject organism to which it is administered. Normally the protein comprises a diagnostic or therapeutic agent. For example, it may comprise a substance used in diagnosis, prevention or treatment of a disease or pathological condition. The protein may comprise a marker or labeling agent e.g. for diagnosis. In the content of this invention the protein normally comprises a therapeutic substance for treating or preventing a pathological condition, especially angiogenesis, for example in treatment of cancer and other tumours, rheumatoid arthritis, diabetic retinopathy, age-related macular degeneration and angiomas. It may for example comprise a toxin, enzyme or a mediator of immunity such as a cytokine.

The protein may be native or recombinant interleukin-12 (IL12). IL12 useful in the invention may be derived from any animal, e.g. human, rodent (e.g. rat, mouse), horse, cow, pig, sheep, dog, etc. . . . Human IL12 is preferred in conjugates for administration to humans. IL12 occurs naturally as a heterodimeric protein composed of a 40 kDa (p40) subunit and a 35 kDa (p35) subunit. The actual molecular weights of the subunits may vary, e.g. when expressed in different species and depending on whether the protein is glycosylated and on the glycosylation pattern. The terms "p40" and "p35" therefore do not imply that the subunits have molecular weights of exactly 40 and 35 kDa respectively. Instead, these terms are used to identify and distinguish the two heterodimeric subunits of IL12, which may more accurately be defined in terms of their amino acid sequences. Heterodimeric IL12 comprises a first and a second polypeptide subunit homologous or identical with or the p40 subunit and p35 subunit of human IL12, respectively. Typically, first subunit of IL12 comprises an amino acid sequence that has at least 60%, 65%, 70%, 75%, 80%, 85%, 90%, 95% or 100% sequence identity with the amino acid sequence of human IL12 subunit p40 as set out in SEQ ID NO: 3. Typically, the second subunit of IL12 comprises an amino acid sequence that has at least 60%, 65%, 70%, 75%, 80%, 85%, 90%, 95% or 100% sequence identity with the amino acid sequence of human IL12 subunit p35 as set out in SEQ ID NO: 4. IL12 in conjugates of the invention retains a biological activity of IL12, e.g. an ability to act as a growth factor for activated T and NK cells, to enhance the lytic activity of NK/lymphokine-activated killer cells, to stimulate production of IFN-γ by resting PMBC, to inhibit angiogenesis (e.g. through the downstream mediator IP-10), and/or to inhibit tumour growth and/or metastasis.

A specific binding member is a member of a pair of molecules that have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other.

The specific binding member normally comprises a molecule having an antigen-binding site. For example, a specific binding member may be an antibody molecule or a non-antibody protein that comprises an antigen-binding site. An antigen binding site may be provided by means of arrangement of complementarity-determining regions (CDRs) on non-antibody protein scaffolds such as fibronectin or cytochrome B etc. [29, 30, 31], or by randomising or mutating amino acid residues of a loop within a protein scaffold to confer binding specificity for a desired target. Scaffolds for engineering novel binding sites in proteins have been reviewed in detail [31]. Protein scaffolds for antibody mimics have been disclosed [32], including proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein.

An advantage of a non-antibody protein scaffold is that it may provide an antigen-binding site in a scaffold molecule that is smaller and/or easier to manufacture than at least some antibody molecules. Small size of a specific binding member may confer useful physiological properties such as an ability to enter cells, penetrate deep into tissues or reach targets within other structures, or to bind within protein cavities of the target antigen.

Use of antigen binding sites in non-antibody protein scaffolds is reviewed in [34]. Typical are proteins having a stable backbone and one or more variable loops, in which the amino acid sequence of the loop or loops is specifically or randomly mutated to create an antigen-binding site having specificity for binding the target antigen. Such proteins include the IgG-binding domains of protein A from *S. aureus*, transferrin, tetranectin, fibronectin (e.g. 10th fibronectin type III domain) and lipocalins. Other approaches include synthetic "Microbodies" (Selecore GmbH), which are based on cyclotides—small proteins having intra-molecular disulphide bonds.

Although, as noted, CDRs can be carried by scaffolds such as fibronectin or cytochrome B (29, 30, 31), the structure for carrying a CDR or a set of CDRs of the invention will preferably be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat et al. [35], and updates thereof, now available on the Internet.

An antibody molecule is an immunoglobulin whether natural or partly or wholly synthetically produced. The term also covers any polypeptide or protein comprising an antibody antigen-binding site.

It is possible to take monoclonal and other antibodies and use techniques of recombinant DNA technology to produce other antibodies or chimeric molecules that retain the specificity of the original antibody. Such techniques may involve introducing DNA encoding the immunoglobulin variable region, or the CDRs, of an antibody to the constant regions, or constant regions plus framework regions, of a different immunoglobulin [37, 38, 39]. A hybridoma or other cell producing an antibody may be subject to genetic mutation or other changes, which may or may not alter the binding specificity of antibodies produced.

As antibodies can be modified in a number of ways, the term "antibody molecule" should be construed as covering any specific binding member or substance having an antibody antigen-binding site with the required specificity. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide are therefore included. Cloning and expression of chimeric antibodies is well known [40, 41].

Further techniques available in the art of antibody engineering have made it possible to isolate human and humanised antibodies. For example, human hybridomas can be made as previously described [36]. Phage display, another established technique for generating specific binding members has been described in detail [36, 42]. Transgenic mice in which the mouse antibody genes are inactivated and functionally replaced with human antibody genes while leaving intact other components of the mouse immune system, can be used for isolating human antibodies [43].

Synthetic antibody molecules may be created by expression from genes generated by means of oligonucleotides synthesized and assembled within suitable expression vectors [44, 45].

It has been shown that fragments of a whole antibody can perform the function of binding antigens. Antibody fragments are preferred in conjugates of the invention owing to their small size and minimised interaction with other molecules and receptors (e.g. Fc receptor). Particularly preferred are single chain Fv molecules (scFv), wherein a VH domain and a VL domain are linked by a peptide linker which allows the two domains to associate to form an antigen binding site [46, 47]. scFv may be stabilised by the incorporation of disulphide bridges linking the VH and VL domains [48].

Another small antigen-binding antibody fragment is a dAb (domain antibody), namely the variable region of an antibody heavy or light chain [28]. VH dAbs occur naturally in camelids (e.g. camel, llama) and may be produced by immunising a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation.

Single domain specific binding members, especially single domain antibodies such as dAbs, may be used in the invention, and are commercially available e.g. from Domantis, Phylos, Pieris and Affibody.

An antigen-binding site is the part of a molecule that binds to and is complementary to all or part of the target antigen. In an antibody molecule it is referred to as the antibody antigen-binding site, and comprises the part of the antibody that specifically binds to and is complementary to all or part of the target antigen. Where an antigen is large, an antibody may only bind to a particular part of the antigen, which part is termed an epitope. An antibody antigen-binding site may be provided by one or more antibody variable domains. Preferably, an antibody antigen-binding site comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen-binding site is specific for a particular epitope that is carried by a number of antigens, in which case the specific binding member carrying the antigen-binding site will be able to bind to the various antigens carrying the epitope.

L19 is a human recombinant antibody specific for the ED-B domain of fibronectin isoform B-FN. This antibody and its sequence have been previously described [20]. Single-chain Fv of L19 has also been described, and is preferentially employed in conjugates of the invention. ScFv(L19) is an scFv comprising an L19 VH domain and an L19 VL domain, wherein the VH and VL are conjoined in a single polypeptide chain by a peptide linker sequence. The VH domain contains VH CDR1, CDR2 and CDR3 sequences, and the VL domain contains VL CDR1, CDR2 and CDR3 sequences, as shown in FIG. 10. The L19 CDR sequences are:

| VH CDR 1 | SFSMS | SEQ ID NO: 25 |
|---|---|---|
| VH CDR 2 | SISGSSGTTYYADSVKG | SEQ ID NO: 26 |
| VH CDR 3 | PFPYFDY | SEQ ID NO: 27 |
| VL CDR 1 | RASQSVSSSFLA | SEQ ID NO: 28 |
| VL CDR 2 | YASSRAT | SEQ ID NO: 29 |
| VL CDR 3 | QQTGRIPPT | SEQ ID NO: 30 |

The VH domain may have an amino acid sequence as set out in SEQ ID NO: 22, and the VL domain may have an amino acid sequence as set out in SEQ ID NO: 23 (FIG. 10). The VH and VL domains are normally joined by a peptide linker such as the 12 residue linker SEQ ID NO: 24 (FIG. 10). Preferably, the scFv(L19) has the amino acid sequence as set out in SEQ ID NO: 5.

BRIEF DESCRIPTION OF THE DRAWINGS

FIG. 8 shows the amino acid sequence SEQ ID NO: 1. The sequence contains, from the N to the C terminus:
(i) a signal peptide;
(ii) human IL12 p40 subunit (shown broken underlined—SEQ ID NO: 3);
(iii) peptide linker (SEQ ID NO: 15);
(iv) scFv(L19) (shown underlined—SEQ ID NO: 5); and
(v) myc;
i.e. signal peptide-human p40-linker-L19-myc. In the encoding nucleic acid sequence we used, the myc tag was followed by three stop codons.

FIG. 9 shows the amino acid sequence SEQ ID NO: 2. The sequence contains, from the N to the C terminus:
(i) a signal peptide;
(ii) scFv(L19) (shown underlined—SEQ ID NO: 5);
(iii) peptide linker (SEQ ID NO: 15);
(iv) human IL12 p35 subunit (shown broken underlined—SEQ ID NO: 4); and
(v) 6His-tag;
i.e. signal peptide-L19-linker-human p35-6×His. In the encoding nucleic acid sequence we used, the six histidines were followed by three stop codons.

FIG. 10 shows the amino acid sequence of scFv(L19) (SEQ ID NO: 5). The VH and VL domains are shown separately (SEQ ID NO: 22 and SEQ ID NO: 23, respectively). The CDR1, 2 and 3 sequences in both the VH and VL domain are shown underlined. The VH and VL domains are separated by a 12 residue peptide linker sequence (SEQ ID NO: 24).

Figure 11:
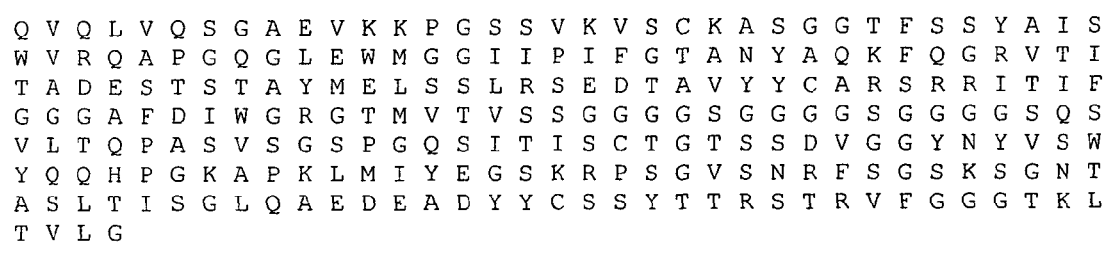

FIG. 11 shows the amino acid sequence of anti-tenascin-C scFv TN11 (SEQ ID NO: 21).

Aspects and embodiments of the invention will now be exemplified in the following experimental section.

EXAMPLES

Here we describe production and characterisation of IL12-L19 conjugates in three different formats, demonstrating the marked superiority of the format as claimed herein for in vivo targeting.

Figure 1:
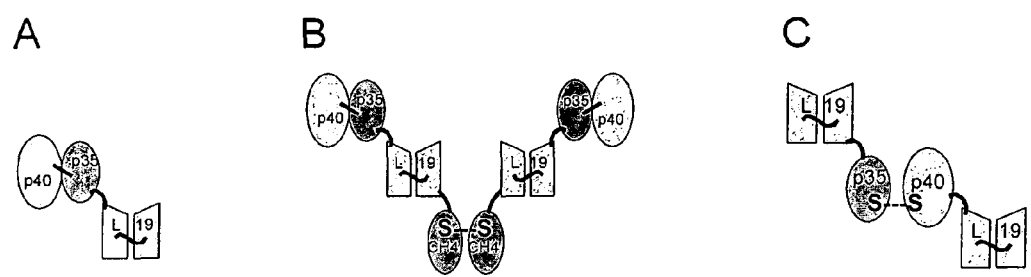
FIG. 1 (A) shows scIL12-scFv(L19); (B) shows scIL12-SIP(L19) homodimer; (C) shows p40-scFv(L19)/scFv(L19)-p35 heterodimer.

The three formats, as illustrated in FIG. 1 A, B and C, respectively, are scIL12-scFv(L19), scIL12-SIP(L19) homodimer and p40-scFv(L19)/scFv(L19)-p35 heterodimer.

scIL12-scFv(L19), depicted in FIG. 1 A, is a fusion protein of scIL12 and scFv(L19). This conjugate is monovalent owing to the single scFv antigen-binding site per molecule.

The scIL2-SIP(L19) homodimer, depicted in FIG. 1 B, is a homodimer of two fusion proteins, each fusion protein containing scIL12, scFv(L19) and the CH4 domain of human IgE, respectively. The conjugate is dimerised through disulphide linkage between the two CH4 domains, forming a miniantibody or SIP structure. This conjugate is bivalent owing to the presence of two scFv(L19) antigen-binding sites per molecule.

The p40-scFv(L19)/scFv(L19)-p35 heterodimer, illustrated in FIG. 1 C, is a heterodimer of two different fusion proteins. The first fusion protein contains the human IL12 p40 subunit fused to the N terminus of scFv(L19) through a 6 amino acid peptide linker GSADGG (SEQ ID NO: 15). The second fusion protein contains scFv(L19) fused to the N terminus of human IL12 p35 subunit through a 6 amino acid peptide linker GSADGG (SEQ ID NO: 15). The two fusion proteins are heterodimerised through disulphide linkage between the p40 and p35 subunit, to form the heterodimeric p40-scFv(L19)/scFv(L19)-p35. The conjugate is bivalent, owing to the presence of two scFv(L19) antigen-binding sites per molecule.

scIL12-scFv(L19) without a FLAG Tag

Since the original fusion protein as previously described [15] was cloned with a C-terminal FLAG tag ("scIL12-scFv (L19)-FLAG"), we should consider the possibility that the tyrosine-containing FLAG tag may contribute to artefacts in biodistribution experiments. When the tyrosines of the protein are radio labelled, the solvent-exposed tyrosine of the FLAG tag may be iodinated as well. The FLAG tag may be later proteolysed in vivo. In order to better study the tumour-targeting properties of this fusion protein, we cloned and expressed scIL12-scFv(L19) fusion protein without a FLAG tag.

Cloning and expression of scIL12-scFv(L19)

The DNA-fragment for scIL12-scFv(L19) was amplified using the pCH33 vector containing the gene for scIL12-scFv (L19)-FLAG [15] as a template. The PCR reaction was performed with the primer sp40backEco (5' ccg gaattc atg tgt cct cag aag cta acc atc 3') (SEQ ID NO: 6), which anneals to the endogenous secretion sequence of p40 and appends a restriction site for the endonuclease EcoR1 to its 5'end, and the primer L19stopNotfor (5' ttt tcc ttt t gcggccgc cta tca tca ttt gat ttc cac ctt ggt ccc 3') (SEQ ID NO: 7) appending 3 stop codons followed by a restriction side for the endonuclease Not1 to the 3'end of the scIL12-L19 fusion protein, and thereby deleting the FLAG tag. The DNA fragment was cloned into the mammalian cell expression vector pcDNA3.1 (+) vector (Invitrogen, Basel, Switzerland), using the EcoR1 and Not1 restriction sites of the vector.

Figure 2:
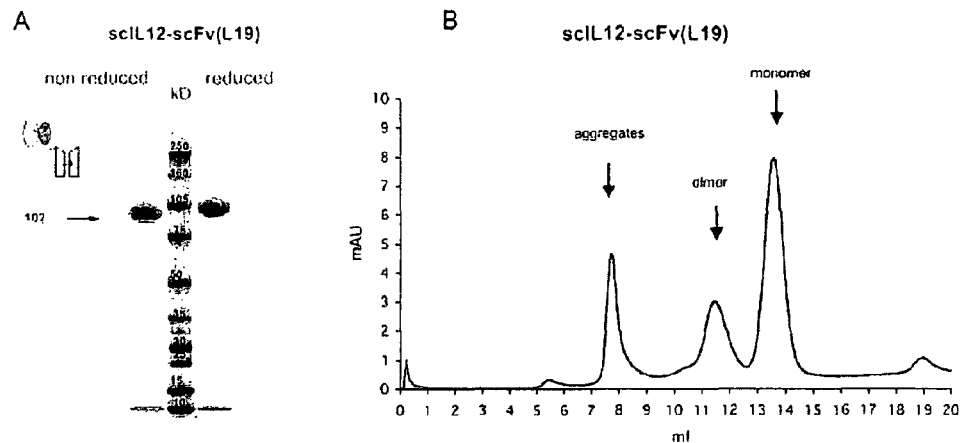
FIG. 2 (A) shows SDS-PAGE analysis of the scIL12-scFv (L19) fusion protein under reduced and non reduced conditions; (B) shows gel filtration profile of the scIL12-scFv(L19) fusion protein under native conditions showing dimers.

HEK 293 cells were transfected with the vector and stable transfectants selected in the presence of G418 (500 µg/ml). Clones of G418-resistant cells were screened for the expression of the fusion protein by ELISA, using recombinant ED-B domain of human fibronectin as an antigen. The fusion protein was purified from cell culture medium by affinity chromatography over antigen column as described previously [19, 20] and desalted by dialysis over night at 4° C. The fusion protein was frozen in aliquots at −20° C. The size of the scIL12-scFv(L19) fusion protein was analyzed under reducing and non reducing conditions on SDS-PAGE and under native conditions by FPLC gel filtration on a Superdex S-200 column (Amersham Pharmacia Biotech) (FIG. 2). Unlike the monomeric original scIL 2-scFv(L19)-FLAG fusion protein, about one third of the IL12-L19 protein fraction showed to be a dimer.

Characterization of scIL12-scFv(L19)

Figure 3:
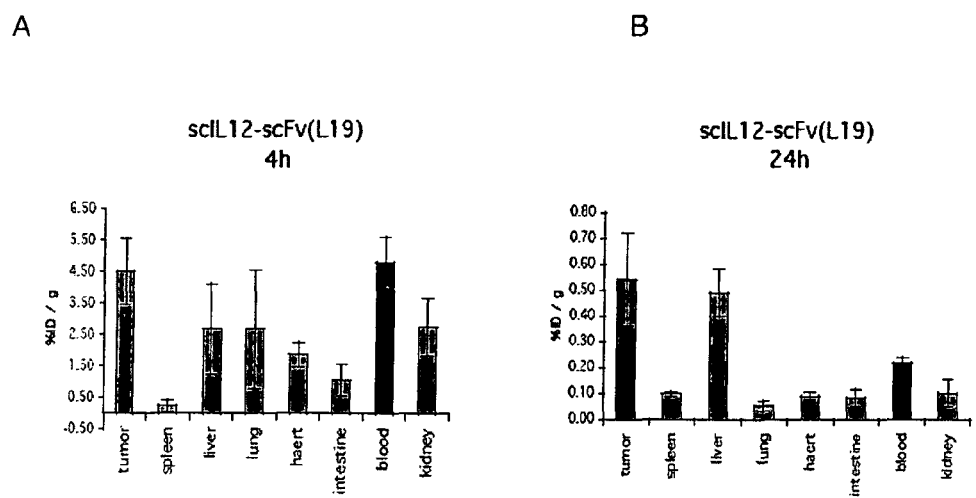
FIG. 3 shows in vivo targeting of scIL12-scFv(L19) evaluated with biodistribution experiments. Accumulation is expressed in % injected dose per gram of tissue (% ID/g) after (A) 4 and (B) 24 h. The tissues represented are (from left to right): tumour, spleen, liver, lung, heart, intestine, blood and kidney.

The in vivo targeting of scIL 2-scFv(L19) without a FLAG tag was evaluated with biodistribution experiments. Therefore the monomeric fraction of the fusion protein was purified by FPLC gel filtration over a Superdex S-200 column. The fraction was iodinated immediately after purification and injected in 129SvEv immunocompetent mice bearing F9 murine teratocarcinoma tumours. Mice were sacrificed 4 and 24 hours after injection, the organs were weighed and the radioactivity counted. The accumulation in representative organs and the tumour was expressed in % injected dose per gram of tissue (% ID/g) (FIG. 3). After 24 hours no accumulation at the tumour site could be observed. Therefore we consider the flag tag did not disturb the biodistribution results.

scIL12-SIP(L19) Homodimer

The tumour targeting properties of scFv(L19) have been shown to be improved when scFv(L19) was dimerised thanks to the CH4 domain of human IgE, building a mini-antibody structure, also termed "small immune protein" or SIP. The tumour targeting properties of SIP(L19) have been previously described [21]. Therefore, we constructed a homodimer of scIL12-SIP(L19) to test whether this format would also improve targeting of IL12 to tumours.

We constructed the scIL12-SIP(L19) fusion protein by fusing the CH4 domain of a human IgE immunoglobulin at the c-terminus of the scIL12-scFv(L19)-FLAG fusion protein [22].

Cloning and Expression of scIL12-L19-SIP Homodimer

The fusion of the CH4 domain to the c-terminus of the scIL12-L19 fragment was performed by one round of PCR and inserting the PCR fragment in a vector already containing the CH4 domain.

The scIL12-scFv(L19) fragment was amplified from the pCH33 vector containing the gene for scIL12-scFv(L19)-FLAG [15]. The restriction sites were exchanged with the primer sp40backHind (5' ccgta aagctt atg tgt cct cag aag cta acc atc 3') (SEQ ID NO: 8) that anneals at the 5' end of the p40 secretion sequence and changes the EcoR1 to a HindIII restriction site, and the primer L19forAgeIBsp (5' tgt ggg accggt ttt gat ttc cac ctt ggt ccc 3') (SEQ ID NO: 9) annealing at the 3' end, deleting the FLAG tag and introducing an Age1 restriction site which provides cohesive ends with BspE1. Once ligated the Age1/BspE1 restriction site is not recleavable with BspE1 any more. This step is necessary because the scIL12 sequence contains a BspE1 restriction site. Using the endonucleases HindIII and BspE1 the fragment was now cloned in a mammalian cell pcDNA3.1(+) expression vector already containing a CH4 domain with a BspE1 restriction site at its 5'end [21].

Figure 4:
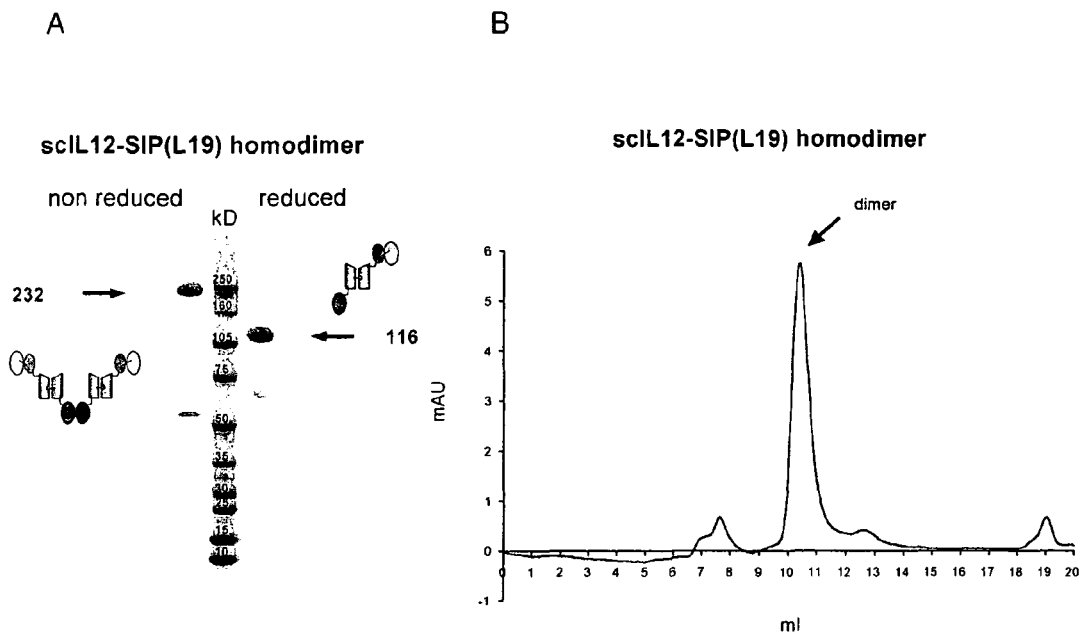
FIG. 4 (A) shows SDS-PAGE analysis of the scIL12-SIP (L19) fusion protein under reduced and non reduced conditions; (B) shows gel filtration profile of the scIL12-SIP(L19) fusion protein under native conditions showing it to be a dimer.

The transfection, expression and purification procedure for the scIL12-SIP(L19) was performed as described above for the scIL12-scFv(L19) fusion protein. The size of the IL12-SIP(L19) fusion protein was as well analyzed under reducing and non reducing conditions on SDS-PAGE and under native conditions by FPLC gel filtration on a Superdex S-200 column (FIG. 4).

Characterization of scIL12-SIP(L19) Homodimer

Figure 5:
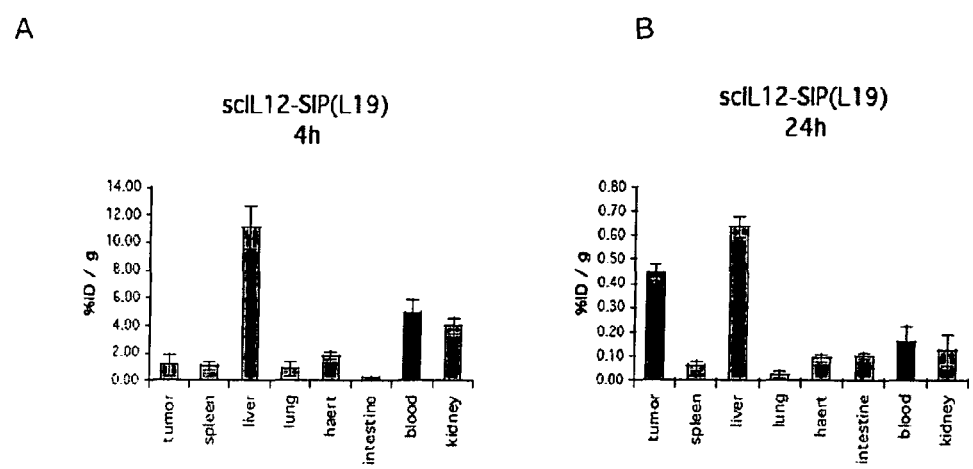
FIG. 5 shows in vivo targeting of scIL12-SIP(L19) evaluated with biodistribution experiments and the accumulation expressed in % injected dose per gram of tissue (% ID/g) after (A) 4 and (B) 24 h. The tissues represented are (from left to right): tumour, spleen, liver, lung, heart, intestine, blood and kidney.

The scIL12-SIP(L19) protein was purified in a second step over a gel filtration Superdex S-200 column and the dimer fraction radio iodinated immediately after collection. The labelled protein was injected in 129SvEv immunocompetent mice bearing F9 murine teratocarcinoma tumours. The mice were sacrificed 4 and 24 hours after injection, the organs were weighed and the radioactivity counted. The accumulation in representative organs and the tumour was expressed in % injected dose per gram of tissue (% ID/g) (FIG. 5). Although the scIL12-SIP(L19) protein displayed an improved binding to ED-B in BIAcore, an increased tumour uptake could not be observed and the tumour uptake remained poor.

p40-scFv(L19)/scFv(L19)-p35 Heterodimer

The p40-scFv(L19)/scFv(L19)-p35 heterodimer consists of two subunits. One contains a scFv(L19) fragment, fused at the N-terminal extremity of the p35 subunit of IL12 (scFv (L19)-p35). In the second, the subunit p40 of IL12 is fused at the N-terminal end of scFv(L19) (p40-scFv(L19)). The fusion proteins then build the heterodimeric p40-scFv(L19)/scFv(L19)-p35 by means of the disulphide bonds between p40 and p35.

This heterodimeric antibody-cytokine fusion protein conjugate is expected to have a size of 114 kD when unglycosylated. Owing to different glycosylation states, the molecular weight of the conjugate may vary according to the species in which it is expressed, owing to different glycosylation patterns. Theoretical sizes for the fusion proteins, based on length of DNA sequence without post-translational glycosylation, were 65 kDa for p40-L19, 49 kDa for L19-p35 and 114 kDa for the heterodimer p40-L19/L19-p35.

Cloning and Expression of p40-scFv(L19)/scFv(L19)-p35

The two subunits p40-scFv(L19) and scFv(L19)-p35 were cloned separately into two different vectors, the first containing a myc tag for detection and the second containing a his tag for detection.

The p40-scFv(L19)-myc fragment was produced by PCR assembly using as templates the pCH33 vector containing the gene encoding the scIL12-scFv(L19)-FLAG protein [15] and the pLB vector containing the gene encoding the SIP(L19) fragment [21]. A first fragment A containing the p40 moiety was constructed using pCH33 as a template. The PCR reaction was performed with a first primer HindSp40back (5' ccc aagctt atg tgt cct cag aag cta acc atc 3') (SEQ ID NO: 10) annealing to the secretion sequence of the p40 subunit of IL12 introducing a restriction site for the endonuclease HindIII at its 5'end and with a second primer Sp40HaLifor (5' acc tcc atc agc gct tcc gga tcg gac cct gca gg 3') (SEQ ID NO: 11) annealing to the 3'end of p40, appending a part of the linker (GSADGG) to be fused to the second fragment B. This fragment B contributing the scFv(L19) moiety was constructed in 2 rounds of PCR using the template pLB with a first primer LinkL19back (5' gga agc gct gat gga ggt gag gtg cag ctg ttg gag tc 3') (SEQ ID NO: 12) annealing to the 5'end of the scFvL19 appending a part of the linker (GSADGG) (SEQ ID NO: 15) and a second primer L19mycstoBamfor (5' att cag atc ctc ttc tga gat gag ttt ttg ttc ttt gat ttc cac ctt ggt ccc ttg 3') (SEQ ID NO: 13) annealing to the 3'end of the scFv(L19) and appending a C-terminal myc tag. This fragment was finished in a second round of PCR using the primer LinkL19back and a third primer mycstoBamfor (5' cgc ggatcc cta tca tca att cag atc ctc ttc tga gat gag ttt 3') (SEQ ID NO: 14) appending 3 stop codons and a restriction site for BamH1 to the 5'end of fragment B. Using both fragments as templates a PCR assembly with the primers HindSp40back and mycstoBamfor was performed to fuse the p40 fragment to the N-terminus of the antibody fragment scFv(L19) connected by the flexible linker GSADGG producing the fragment p40-GSADGG-L19-myc. Using HindIII and BamH1 as restriction sites the fragment was then cloned into a mammalian expression vector pcDNA3.1+/Hygro providing a hygromycine resistance for selection. CHO cells were transfected with the vector and stable transfectants were selected with hygromycine (500 µg/ml). Positive clones were screened with ELISA using recombinant ED-B as an antigen and anti-myc antibody for detection. The protein was expressed and purified from the cell culture medium by antigen affinity chromatography as described previously [19, 20] and desalted by dialysis over night at 4° C. The fusion protein frozen in aliquots at −20° C. An SDS PAGE size analysis showed the protein to be approximately 50% monomers in two different glycosylation states and about 50% homodimer [23].

The scFv(L19)-p35-His fragment was produced by PCR assembling as well using the same plasmids pCH33 and pLB as templates. A first fragment C corresponding to the scFv (L19) moiety was constructed from the template pLB with a first primer EcoLonSL19back (5' ccg gaattc gct tgt cga cca tgg gct g 3') (SEQ ID NO: 16) annealing to the secretion sequence of the scFvL19 introducing a restriction site for the endonuclease EcoR1 at its 5'end and a second primer L19HaLifor (5' acc tcc atc agc gct tcc ttt gat ttc cac ctt ggt ccc 3') (SEQ ID NO: 17) annealing to the 3'end of scFv(L19), introducing a part of the linker (GSADGG). A second fragment D containing the p35 moiety was constructed in two rounds of PCR using the template pCH33 with a first primer HaLip35back (5' gga agc gct gat gga ggt agg gtc att cca gtc tct gga 3') (SEQ ID NO: 18) annealing to the 5'end of the mature p35 subunit appending a part of the linker (GSADGG) to its 5'end and a second primer p35hisfor (5' gtg atg gtg atg atg atg ggc gga gct cag ata gcc 3') (SEQ ID NO: 19) annealing to the 3'end of the p35 subunit appending a his tag. In a second round of PCR 3 stop codons and a restriction site for Not1 were appended to the 3'end of fragment D using the primer HaLip35back and a third primer p35hisstoNotlfor (5' ttt tcc ttt t gcggccgc cta tca tca gtg atg gtg atg atg atg ggc 3') (SEQ ID NO: 20). The p35 cytokine subunit was now fused to the c-terminus of the scFv(L19) fragment by PCR assembly using the primers EcoLonSL19back and p35hisstoNotlfor producing L19-GSADGG-p35-his. The fragment was now cloned into a pcDNA 3.1 mammalian expression vector providing a neomycine resistance using the EcoR1 and Not1 restriction sites. HEK 293 cells were transfected and stable transfectants selected with G418 (500 µg/ml). Transfected cells were screened for resistant clones expressing the fusion protein by ELISA, using human recombinant EDB as an antigen and anti-his antibody for detection. The fusion protein was purified from the cell culture medium by affinity chromatography over an antigen column as described previously [19, 20] desalted by dialyzation over night at 4° C. An SDS PAGE analysis showed the expression to be very week and the protein was shown to consist of monomers, dimers and higher order oligomers.

Figure 6:
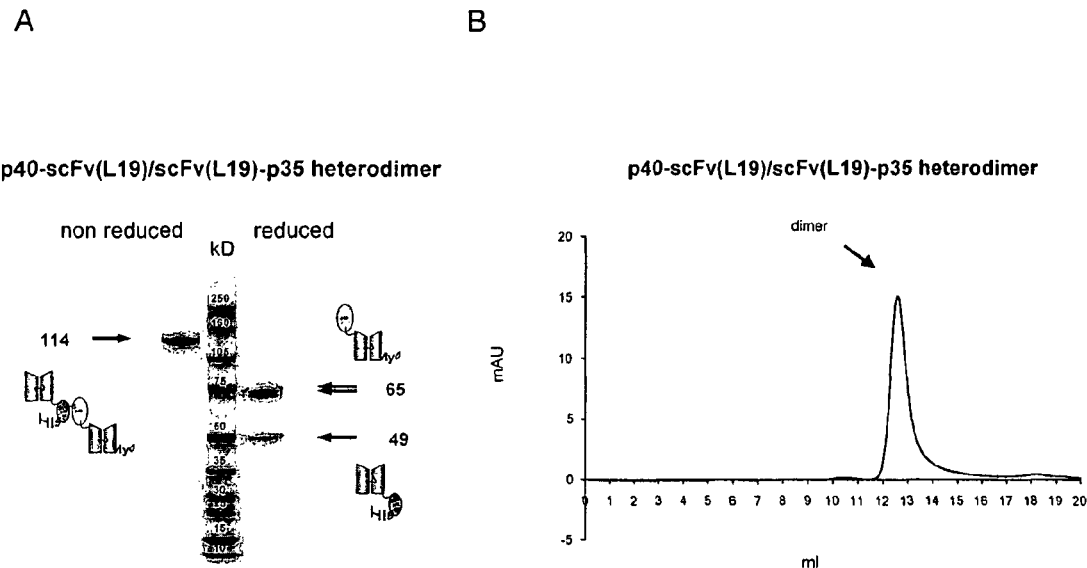
FIG. 6 (A) shows SDS-PAGE analysis of the p40-scFv (L19)/scFv(L19)-p35 fusion protein under reduced and non reduced conditions; (B) shows gel filtration profile of the p40-scFv(L19)/scFv(L19)-p35 fusion protein under native conditions showing to be a dimer.

The cotransfection of HEK 293 cells with the two vectors coding for scFv(L19)-p35 and p40-scFv(L19) was then performed simultaneously. The selection for stable transfectants that contain both fusion proteins was performed with G418 (500 µg/ml) and hygromycine (500 µg/ml). Cells were screened for expression of both proteins with ELISA using recombinant EDB as an antigen and anti-myc antibody as well as anti-his antibody for detection. The fusion proteins were purified in a first step by affinity chromatography over an ED-B antigen column as described previously [19, 20] and desalted by dialysis over night at 4° C. This first fraction was then purified in a second step over a HisTrap HP 1 ml $Ni^{2+}$ column (Amersham Biosciences) washing away the free p40-scFv(L19) fragments not bound in the heterodimer (p40-scFv (L19)/scFv(L19)-p35). For storage, 0.1% Tween 80 was added to the protein that was then frozen in aliquots at −80° C. An SDS PAGE analysis showed under non reduced conditions the protein to be a dimer in two glycosylation states and under reduced conditions the two hetero monomers of different sizes where of the p40-L19 monomer appears in its two different glycosylation states. By performing gel filtration with a Superdex S-200 column the protein showed to be a pure dimer under native conditions (FIG. 6).

Characterization of p40-scFv(L19)/scFv(L19)-p35

The correct folding of the fusion protein and building of the correct disulfide bonds were determined by the IL12 activity of the purified heterodimeric protein.

The IL-12 activity was determined by performing a T cell proliferation assay [24]. In brief, resting human peripheral blood monocytes (PBMC) were cultured with mitogen (phytohemagglutinin (PHA) and IL-2) for 3 days and then incubated with serial dilutions of either fusion proteins or commercially available, recombinant, murine IL-12 as a standard (R&D Systems Europe Ltd, Abingdon, United Kingdom). Proliferation was subsequently measured by [$^3$H]thymidine incorporation.

Figure 7:
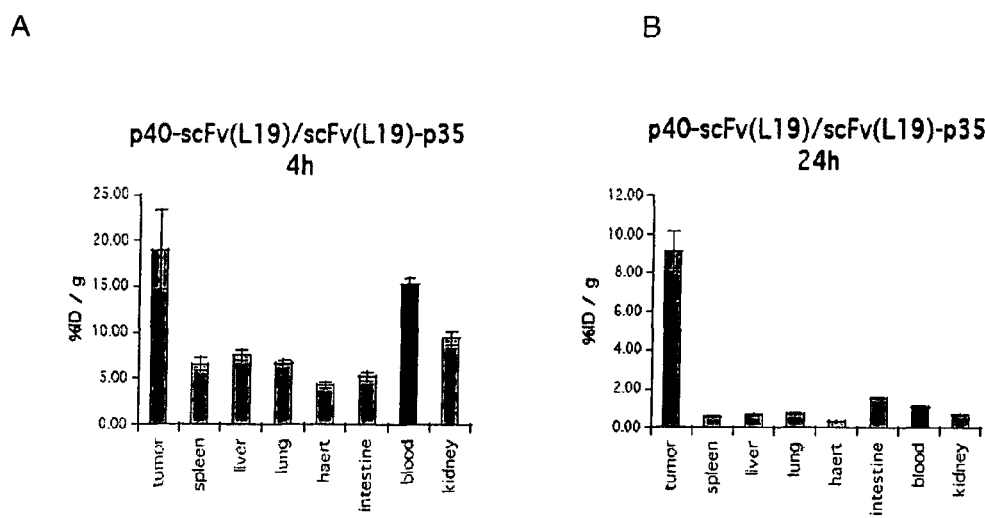
FIG. 7 shows in vivo targeting of p40-scFv(L19)/scFv (L19)-p35 evaluated with biodistribution experiments and the accumulation expressed in % injected dose per gram of tissue (% ID/g) after (A) 4 and (B) 24 h. The tissues represented are (from left to right): tumour, spleen, liver, lung, heart, intestine, blood and kidney.

Biodistribution experiments were performed with the p40-scFv(L19)/scFv(L19)-p35 protein that was purified on a FPLC gelfiltration Superdex S-200 column and radioiodinated. The labelled protein was injected in 129SvEv immunocompetent mice bearing F9 murine teratocarcinoma tumours. The mice were sacrificed 4 and 24 hours after injection, the organs were weighed and the radioactivity counted. The accumulation in representative organs and the tumour was expressed in % injected dose per gram of tissue (% ID/g). With the heterodimeric format we achieved a tumour uptake of almost 10% at 24 hours (FIG. 7).

REFERENCES

All references cited are specifically incorporated herein by reference.
1. Viti, F., et al., Cancer Res, 1999. 59(2): p. 347-52.
2. Birchler, M., et al., Nat Biotechnol, 1999. 17(10): p. 984-8.
3. Nilsson, F., et al., Cancer Res, 2001. 61(2): p. 711-6.
4. Tsung, K., et al., J Immunol, 1997. 158(7): p. 3359-65.
5. Brunda, M. J., et al., J Exp Med, 1993. 178(4): p. 1223-30.
6. Rodolfo, M. and M. P. Colombo, Methods, 1999. 19(1): p. 114-20.
7. Nastala, C. L., et al., J Immunol, 1994. 153(4): p. 1697-706.
8. Atkins, M. B., et al., Clin Cancer Res, 1997. 3(3): p. 409-17.
9. Car, B. D., et al., Toxicol Pathol, 1999. 27(1): p. 58-63.
10. Jain, R. K. a. B. L. T., Cancer Res., 1988.48: p. 7022-32.
11. Folkman, J., Nat Med, 1995.1 (1): p. 27-31.
12. Voest, E. E., et al., J Natl Cancer Inst, 1995. 87(8): p. 581-6.
13. Duda, D. G., et al.,. Cancer Res, 2000. 60(4): p. 1111-6.
14. Neri, D., and Melkko, S., U.S. patent application Ser. No. 10/382,107,
15. Halin, C., et al., Nat Biotechnol, 2002. 20(3): p. 264-9.
16. Santimaria, M., et al., Clin Cancer Res, 2003. 9(2): p. 571-9.
17. Gillies, S., U.S. Pat. No. 6,838,260. 2005.
18. Carnemolla, B., et al., Blood, 2002. 99(5): p. 1659-65.
19. Neri, D., et al., Nat. Biotechnol., 1996. 14: p. 485-490.
20. Tarli, L., et al., Blood, 1999. 94(1): p. 192-8.
21. Borsi, L., et al., Int J Cancer, 2002. 102(1): p. 75-85.
22. Li, E., et al., Protein Eng, 1997. 10(6): p. 731-6.
23. Trinchieri, G., Nat Rev Immunol, 2003. 3(2): p. 133-46.
24. Gately, M. K., R. Chizzonite, and H. D. Presky, Current Protocols in Immunology, 1995. 6.16.1-6.16.15 (John Wiley & Sons).
25. WO01/62298 PCT/IB01/00383.
26. Ledermann J. A. et al. (1991) Int J. Cancer 47: 659-664
27. Bagshawe K. D. et al. (1991) Antibody, Immunoconjugates and Radiopharmaceuticals 4: 915-922.
28. Holt et al (2003) Trends in Biotechnology 21, 484-490
29. Haan & Maggos (2004) BioCentury, 12(5): A1-A6.
30. Koide et al. (1998) Journal of Molecular Biology, 284: 1141-1151.
31. Nygren et al. (1997) Current Opinion in Structural Biology, 7: 463-469.
32. WO/0034784
33. WO00/63699
34. Wess, L. In: BioCentury, The Bernstein Report on BioBusiness, 12(42), A1-A7, 2004.
35. Kabat, E. A. et al, Sequences of Proteins of Immunological Interest. $4^{th}$ Edition. US Department of Health and Human Services. 1987
36. Kontermann, R & Dubel, S, *Antibody Engineering*, Springer-Verlag New York, LLC; 2001, ISBN: 3540413545.
37. EP-A-184187
38. GB 2188638A
39. EP-A-239400
40. EP-A-0120694
41. EP-A-0125023
42. International patent application WO92/01047
43. Mendez, M. et al. (1997) Nature Genet, 15(2): 146-156.
44. Knappik et al. J. Mol. Biol. (2000) 296, 57-86
45. Krebs et al. Journal of Immunological Methods 254 2001 67-84
46. Bird et al, Science, 242, 423-426, 1988
47. Huston et al, PNAS USA, 85, 5879-5883, 1988
48. Reiter, Y. et al, Nature Biotech, 14, 1239-1245, 1996
49. Ko et al., *J. Immunother.* 27(3):232-9 May-June 2004
50. King D M, et al. J Clin Oncol. 2004 November 15; 22(22):4463-73. Epub 2004 October 13.
51. Neal Z C, et al. Clin Cancer Res. 2004 July 15; 10(14): 4839-47

The invention claimed is:

1. A conjugate comprising:
   (i) a native or recombinant, full-length, mammalian IL 12 p35 subunit conjugated downstream of a first antibody molecule as a first fusion protein, wherein said IL 12 p35 subunit comprises an amino acid sequence that has at least 95% sequence identity with the amino acid sequence of human IL 12 p35 subunit as set out in SEQ ID NO: 4; and
   (ii) a native or recombinant, full-length, mammalian IL 12 p40 subunit conjugated upstream of a second antibody molecule as a second fusion protein, wherein said IL 12 p40 subunit comprises an amino acid sequence that has at least 95% sequence identity with the amino acid sequence of human IL 12 p40 subunit as set out in SEQ ID NO: 3, wherein the first and second antibody molecules are single chain Fv (scFv) molecules, wherein at least one of said first and second antibody molecules specifically binds to an extracellular matrix component associated with at least one of neoplastic growth and angiogenesis, and wherein (i) and (ii) are linked through heterodimerization of the p35 and p40 subunits.

2. A conjugate according to claim 1, wherein the p35 and p40 subunits of the IL 12 heterodimer are covalently linked through a disulphide bond.

3. A conjugate according to claim 1, wherein the conjugate has a molecular weight of 250,000 Da or less, said molecular weight being calculated as the expected molecular weight of the conjugate without glycosylation.

4. A conjugate according to claim 3, wherein the conjugate has a molecular weight of 150,000 Da or less, said molecular weight being calculated as the expected molecular weight of the conjugate without glycosylation.

5. A conjugate according to claim 4, wherein the conjugate has a molecular weight of 120,000 Da or less, said molecular weight being calculated as the expected molecular weight of the conjugate without glycosylation.

6. A conjugate according to claim 1, wherein the first and second antibody molecules are identical to each other.

7. A conjugate according to claim 1, comprising an IL 12 heterodimer conjugated to and interposed between two scFv antibody molecules; wherein the p35 subunit has the amino acid sequence set out in SEQ ID NO: 4 and is conjugated downstream of a first scFv as a first fusion protein; and the p40 subunit has the amino acid sequence set out in SEQ ID NO: 3 and is conjugated upstream of a second scFv as a second fusion protein.

8. A conjugate according to claim 1, wherein the extracellular matrix component is fibronectin ED-B.

9. A conjugate according to claim 1, wherein the extracellular matrix component is a tenascin-C isoform.

10. A method of producing a conjugate according to claim 1, comprising:
    expressing the first and second fusion proteins; and
    conjugating the p35 and p40 subunits to form the IL 12 heterodimer.

11. A method according to claim 10, comprising expressing the first and second fusion proteins in a cell containing a nucleic acid encoding both fusion proteins.

12. A composition comprising
    a first nucleic acid molecule comprising a nucleotide sequence encoding a fusion protein, wherein the fusion protein comprises a first antibody molecule conjugated downstream of a native or recombinant IL 12 p40 subunit, wherein the subunit comprises an amino acid sequence that has at least 95% sequence identity with the amino acid sequence of human IL 12 subunit p40 as set out in SEQ ID NO: 3; and
    a second nucleic acid molecule comprising a nucleotide sequence encoding a fusion protein, wherein the fusion protein comprises a second antibody molecule conjugated upstream of a native or recombinant IL 12 p35 subunit, wherein the subunit comprises an amino acid sequence that has at least 95% sequence identity with the amino acid sequence of human IL 12 subunit p35 as set out in SEQ ID NO: 4,
    wherein the first and second antibody molecules are single chain Fv (scFv) molecules and wherein at least one of said first and second antibody molecules specifically binds to an extracellular matrix component associated with at least one of neoplastic growth and angiogenesis.

13. A host cell containing a first and a second nucleic acid molecule as defined in claim 12.

* * * * *